(12) United States Patent
Fischinger et al.

(10) Patent No.: US 6,290,963 B1
(45) Date of Patent: Sep. 18, 2001

(54) ANTI-HIV COMPOSITIONS CONTAINING NATIVE AND RECOMBINANT PEPTIDES

(75) Inventors: Peter J. Fischinger, Baltimore; Flossie Wong-Stall, Rockville; Robert C. Gallo, Bethesda, all of MD (US); Thomas J. Matthews; Dani P. Bolognesi, both of Durham, NC (US); Gerard W. Robey, Third Lake, IL (US); Kai Krohn; Annamarie Ranki, both of Tampere (FI)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/314,664

(22) Filed: Feb. 23, 1989

Related U.S. Application Data (63) Continuation-in-part of application No. 06/933,372, filed on Nov. 21, 1986, now abandoned, which is a continuation-in-part of application No. 06/898,974, filed on Aug. 22, 1986, now abandoned, which is a continuation-in-part of application No. 07/168,088, filed on Mar. 11, 1988, now abandoned.

(51) Int. Cl.[7] .................................................. A61K 39/21
(52) U.S. Cl. ..................... 424/188.1; 424/89; 424/184.1; 424/204.1; 424/207.1; 424/208.1; 435/5; 530/350
(58) Field of Search ........................ 530/350; 424/184.1, 424/188.1, 204.1, 207.1, 208.1; 435/5

(56) References Cited

U.S. PATENT DOCUMENTS

| 4,725,669 | * | 2/1988 | Essex et al. ........................... 530/322 |
| 5,019,387 | * | 5/1991 | Haynes et al. ........................... 424/89 |
| 5,142,025 | * | 8/1992 | Putney et al. ........................... 530/350 |

OTHER PUBLICATIONS

Brown, "AIDS Vaccine Trials Viewed with Caution". Wash. Post Newspaper Jun. 10, 1993.*
Cohen "Jitters Jeopardize AIDS Vaccine Trials". Science 262:980–981, 1993.*
Fox, "No Winners Against AIDS", Bio/Technology vol. 12:128, 1994.*
Robey, et al. : Characterization of envelope and core . . . : Science: vol. 228: pp. 593–595, May 1985.*
Crowl, et al, 1985, Cell 41: 979–986.*
Lasky, et al, 1986, Science 233:209–212.*
Chang, et al, 1985, Biotechnology 3:905–909.*
Putney et al., 1986, Science 234: 1392–1395.*
Crowl, et al., 1985, "HTLV–III Gene Products Synthesized . . . " Cell 41:979–986.*
Lasky, et al., 1986, "Neutralization of the AIDS Retrovirus . . . " Science 233: 209–212.*
Chang, et al., 1985 "Detection of and bodies to Human . . . " Biotechnology 3: 905–909.*
Putney, et al., 1986 "HTLV–III/LAN–Neutralizing Antibodies to an *E. coli*. . . . " Science 234:1392–5.*
Starcich, et al., 1986 Identification and Characterization of Conserved . . . . Cell, vol. 45, 637–648.*
Siliciano, et al., 1988, Analysis of Host–Virus Interactions in AIDS . . . , Cell, vol. 54, 561–575.*
Brown, et al.: AIDS vaccine trials viewed with caution: Washington Post Newspaper, Jun. 1993.*
Cohen: Jitters jeopardize AIDS vaccine trials: Science 262: 980–981, 1993.*
Fox: No winners against AIDS: Biotechnology vol. 12: 128, 1994.*

* cited by examiner

Primary Examiner—Jeffrey Stucker
Assistant Examiner—Ulrike Winkler
(74) Attorney, Agent, or Firm—Townsend and Townsend and Crew LLP (57) ABSTRACT

Native and recombinant peptides which elicit anti-HIV immune response are provided.

8 Claims, 5 Drawing Sheets

R-LeuAsnGlnSerValGlu
IleAsnGysThrArgProAsnAsnAsnThrArgLysSerIleArgIleGlnArg
GlyProGlyArgAlaPheValThrIleGlyLysIleGlyAsnMetArgGlnAla
HisCysAsnIleSerArgAlaLysTrpAsnAsnThrLeuLysGlnIleAspSer
LysLeuArgGluGlnPheGlyAsnAsnLysThrIleIlePheLysGlnSerSer
GlyGlyAspProGluIleValThrHisSerPheAsnCysGlyGlyGluPhePhe
TyrCysAsnSerThrGlnLeuPheAsnSerThrTrpPheAsnSerThrTrpSer
ThrLysGlySerAsnAsnThrGluGlySerAspThrIleThrLeuProCysArg
IleLysGlnIleIleAsnMetTrpGlnGluValGlyLysAlaMetTyrAlaPro
ProIleSerGlyGlnIleArgCysSerSerAsnIleThrGlyLeuLeuLeuThr
ArgAspGlyGlyAsnSerAsnAsnGluSerGluIle-R

R = H OR A PEPTIDE FROM A SOURCE OTHER THAN HIV ENVELOPE
    PROTEIN

*FIG. 5.*

ANTI-HIV COMPOSITIONS CONTAINING NATIVE AND RECOMBINANT PEPTIDES

This is a continuation-in-part of application Ser. No. 06/933,372 filed Nov. 21, 1986, now abandoned which is a continuation-in-part of application Ser No. 06/898, 974 filed Aug. 22, 1986 now abandoned. This is also a continuation-in-part of application Ser. No. 168,088 filed Mar. 11, 1988, now abandoned.

The present invention is related to certain substantially pure, antigenic, native and recombinant HIV envelope polypeptides. More particularly, the present invention is related to certain peptides which elicit a cellular immune response and anti-HIV antibodies in a responsive host. The peptides are also useful as diagnostic reagents for detecting HIV infection.

Human immunodeficiency virus (HIV) is a causative factor of acquired immunodeficiency syndrome (AIDS). Effective methods and products to prevent or control HIV infection are still needed.

SUMMARY OF INVENTION

It is, therefore, an object of the present invention to provide native and recombinant HIV envelope proteins which elicit a cellular immune response and/or antibodies against HIV.

It is another object of the present invention to provide anti-HIV compositions and methods of inhibiting HIV infection.

It is a further object of the present invention to demonstrate that purified gp160, gp120, and their deglycosylated analogues interfere with viral infection and block the process of multi-nucleated giant cell formation, i.e. the fusion of uninfected cells with infected cells. It is also shown that deglycosylation of gp120 results in a reagent which nearly eliminates cell fusion or syncytia formation.

It is also shown that native gp120 and recombinant peptides gp160 and PB1 elicit neutralizing antibodies in responsive hosts to which these immunogenic peptides are administered. These immunogens are, therefore, useful as active ingredient in anti-HIV compositions.

Additionally, an increasing body of evidence suggests that the primary mode of transmission of HIV is from infected to uninfected cell. Clearly, the ability of the preparations of the present invention to block the fusion of uninfected to infected cells is of critical importance in understanding the AIDS disease and in devising treatment modalities against the disease.

The complete nucleotide sequence of the envelope gene of HIV is 2,619 nucleotides in length and encodes 873 amino acids. The exterior portion of the envelope glycoprotein constitutes a major immunologic stimulus. It has been shown that a spectrum of diversity exists among the HIV virus isolates; it is the envelope gene which varies most. Furthermore, within the envelope gene, the extracellular region varies considerably more than does the transmembrane region, containing localized regions of high variability and high conservation. This knowledge is useful in developing strategies for combating HIV infection across divergent strains of the virus.

Any of a large number of available host cells may be used to test the infectivity of HIV. The selection of a particular host is dependent upon a number of factors recognized in the art. These include, for example, compatibility with the virus, toxicity of proteins encoded by the virus, ease of recovery of the desired virus or protein product, expression characteristics, bio-safety, and costs. A balance of these factors must be struck with the understanding that not all hosts may be equally effective for expression of a particular recombinant DNA molecule.

Prior to the present invention, AIDS virus variants were propagated in an HT parental cell line, H9. This cell line, as well as other OKT4$^+$ mcell lines capable of immortalizing AIDS virus variants are described in Popovic et al, *Science*, 224:497 (1984) and Sarngadharan et al, *Science*, 224:506 (1984). Of critical concern is evidence that the T-cell tropism of the virus may be acquired behavior resulting from the continual propagation of the virus in T4$^+$ cells (particularly, H9 cells) both in vitro and in vivo. Quantitative titration of an HTLV-III$_B$ isolate on T-cells and monocyte/macrophage (M/M) cells showed a 10,000-fold greater susceptibility on OKT4$^+$ T-cells than M/M cells. Limited evidence suggests that cells other than T-lymphocytes can be infected by the virus. See Montagnier et al, *Science*, Vol. 225, p. 63 (1984); Dalgleish et al, *Nature*, Vol. 312, p. 763 (1984); and Levy et al, *Virology*, Vol. 147, p. 441 (1985).

BRIEF DESCRIPTION OF THE DRAWINGS

Various advantages and objects of the present invention can be better understood when read in light of the drawings wherein.

STATEMENT OF DEPOSIT

Starting materials from which the present invention can be produced have been deposited in the American Type Culture Collection in Rockville, Md. Molecular clone BH10 has been accorded ATCC No. 40125; H9/HTLV-III has been accorded ATCC No. CRL 8543. These deposits shall be viably maintained, replacing if they become non-viable, for a period of 30 years from the date of the deposits, or for 5 years from the last date of request for a sample of the deposits, whichever is longer, and made available to the public without restriction in accordance with the provisions of the law. The Commissioner of Patents and Trademarks, upon request, shall have access to the deposits.

DETAILED DESCRIPTION OF THE INVENTION

Various objects and advantages of the present invention are achieved by compositions and methods of preventing and treating HIV infection. The compositions comprise native HIV envelope proteins or recombinant products corresponding to the HIV specific nucleotide sequences, capable of eliciting a protective immune response in the form of neutralizing antibodies and/or cellular immune response, thus serving as active constituents in an anti-HIV vaccine.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially pure" as used herein means the product is as pure as can be obtained by employing conventional purifying and/or isolation techniques.

Glycoprotein gp120 and deglycosylated protein dg120 of the present invention are isolated from lysates of cells infected with HIV using procedures which are well known to practitioners in the art. See, for example, Robey et al, *PNAS*, 83:7023 –7027 (1986) and Starcich et al, *Cell*, 45:637 (1986). In this manner, glycoprotein gp120 may be purified from HTLV-III$_B$, infected H9 cells (or by the BH10 clone derived from HTLV-III$_B$) by extraction with 0.5% Triton X-100, followed by affinity chromatography using antibody from a strongly seropositive patient, and, finally, by lentil-lectin chromatography. As noted above, these procedures are well known to practitioners in the art, and result in purified gp120.

Both the native and deglycosylated forms of gp120 are within the scope of this invention. These proteins, as well as the recombinant fragment derived from these proteins (described below) are used in the production of neutralizing antibodies—antibodies which neutralize HIV infection in vitro. Furthermore, gp120, in its native and deglycosylated form, is capable of blocking the fusion of cells infected with HIV and uninfected cells. However, the results of the experiments shown in the Examples indicate that glycosylation of the envelope protein is unnecessary for an HIV neutralizing humoral response and that glycosylation is not required to hold the molecule in a conformation necessary to elicit neutralizing antibodies.

The protein backbone of gp120 represents approximately half of its apparent weight (as shown on SDS gels), with the remainder consisting of carbohydrate. The extensive degree of glycosylation is believed to play a role in the determination and accessibility of both binding and neutralizing epitopes. However, endoglycosidase F (Endo F) may optionally be used to remove the bulk of the carbohydrate residues from gp120 purified by affinity chromatography. In the presence of 0.025% SDS, this treatment converts the molecule to a species of about 58 –60 kD, approximately the predicted size of the non-glycosylated polypeptide [Ratner, et al, *Nature*, 313:277 –284 (1985].

While there are many methods of deglycosylating a protein, the following method is illustrative of the process conditions involved. Four µg of purified gp120 in 0.05 sodium acetate, pH 5.5, were incubated with 0.05 unit of endoglycosidase F (Boehringer Mannheim) in the presence and absence of 0.025% SDS for 2 hours at 37° C. The protein was also treated with a higher level of enzyme (0.1 unit) in the absence of detergent. After digestion, the samples were analyzed on a 12% SDS-polyacrylamide gel. The gp120 used was purified from HIV infected cells by affinity chromatography and dialysis against water. After Endo F treatment, deglycosylated gp120 was purified by SDS-polyacrylamide electrophoresis, and 50 µg (in complete Freund's adjuvant) was used to immunize the goat (508). The animal was boosted twice with 50 µg protein, after 21 and 42 days, with the protein in incomplete Freund's adjuvant.

Recombinant Fragments

Figure 5:
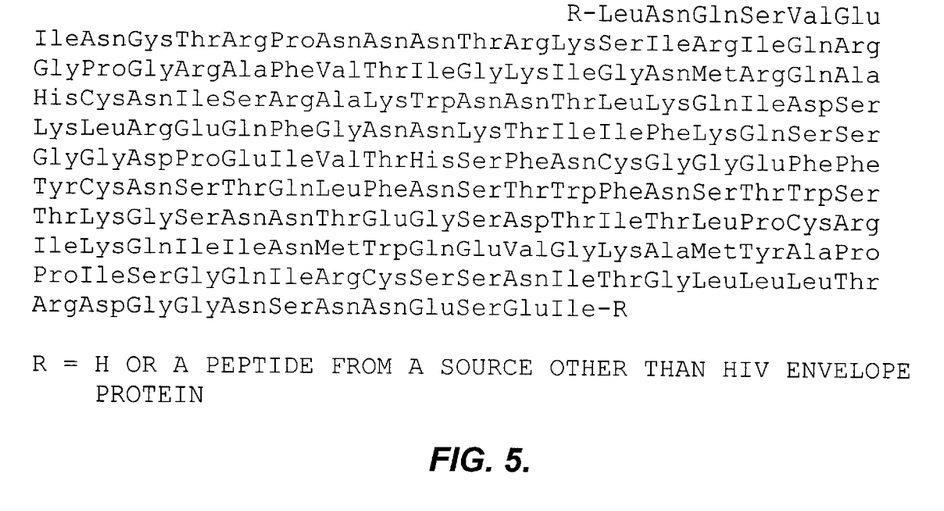
FIG. 5 shows the amino acid sequence of PB1.

The recombinant fragment, PB1 (FIG. 1) is a fusion molecule containing the carboxyl-terminal half of gp120. PB1 contains 180 amino acids encoded by the PvuII to BglII fragment of the HIV env gene The amino acid sequence of PB1 is shown in FIG. 5. In the preferred embodiment, the origin of the HIV DNA for PB1 is the BH10 clone derived from the HTLV-III$_B$ isolate [see Ratner et al, *Nature*, Vol 313, pp. 277 –284 (1985)]. PB1 is expressed from an *E coli* expression vector which has been used to produce other segments of HIV, and PB1 reacts in Western Blot analyses with antibodies in sera from selected AIDS patients. PB1, purified using a single chromatographic step, is over 95% homogeneous as judged by comassie blue staining of SDS-polyacrylamide gels. PB1 constitutes approximately 10% of total cellular protein and is purified using a procedure of cell lysis with lysozyme and glass bead disruption, centrifugation, extraction of the protein from the cell pellet using 6M guanidine hydrchloride, dialysis into 8M urea, and carboxymethyl-sepharose chromatography (Pharmacia) in the presence of 8M urea. PB1 precipitates when the urea is removed by dialysis and the precipitated protein is used as the immunogen. The yield of purified protein from one gram of wet cells is approximately 4 milligrams.

As noted above, one method of producing gp120 is by cleaving HIV molecular clone BH10. This process may alternatively be conducted by cleaving BH10 to produce gp160, and cleaving gp160 to produce gp120. This alternative method has some advantages in that gp160 contains a larger portion of the HIV envelope gene sequences. Also, gp160 is useful in the same manner as gp120 and PB1, i.e. elicits neutralizing antibodies in vitro. Therefore, gp160 is also considered a candidate for a vaccine.

More importantly, gp160 is capable of being expressed in an insect expression system (thus permitting greater and more efficient expression at a lower cost). Expression of the env gene of HIV in insect cells infected with an env-gene-containing vector was studied by immunofluorescence of live cells. Intense membranous staining was obtained with goat antisera against the native, gel purified external glycoprotein of HTLV-III$_B$. (as well as the sera from goats immunized with gp160 from infected cells). In contrast, sera from goats which were immunized with whole infected cells stained equally well the non-infected and infected insect cells, suggesting that these sera contained antibodies against cellular products. Specific but substantially weaker staining was obtained with goat sera to nonglycosylated recombinant peptide PB1, representing the carboxy-terminal part of gp120, expressed in *E. coli*. These data clearly demonstrate that the expressed ENV-gene product is mainly located on the membrane of the infected cell and that it is glycosylated.

As will be readily apparent to a practitioner in the art, the immunogens— both forms of gp120 and gp160, and PB1- are used as the active ingredient in compositions used in the processes of this invention. The active ingredient(s) are present in the composition in immunogenic amount in pharmaceutically acceptable carriers, such as physiologic saline, normal saline, 5% glucose and water, 5% glucose aid saline, or any other physiological medium. The practitioner in the art will understand that this list is representative of the many pharmaceutically acceptable carriers.

Neutralization Table 1 summarizes neutralization titers using the antisera of the present invention, as well as comparative antisera. Two goats (987 and 988) and two rabbits were immunized with 2 and 1 milligrams, respectively, in complete Freund's adjuvant and boosted after three weeks and again after ten days. The immune bleeds were taken one week later. Boosts were with one milligram protein in incomplete Freund's adjuvant. PE3, a recombinant protein produced in the same fashion as PB1, contains the amino-terminal half of native gp120, and is encoded by the DNA from Kpn I to the first Bg1 II site of the env gene of HIV. DG120 is the deglycosylated form of native gp120. Neutralizing titers are expressed as the reciprocal of the serum dilution at which virus infection is 60% of that using pre-immune serum. Although neutralizing titers vary somewhat depending on whether p24 or reverse transcriptase is monitored, the titers of anti-PB1 sera are equivalent to those of anti-gp120 and anti-DG120 sera and also to those of antisera from horses or rhesus monkeys immunized with gp120.

Neutralizing titers of antibodies from HIV infected people vary widely and differ as to whether the patient has AIDS or ARC. The neutralizing titers of the anti-PB1 sera are comparable to those from these individuals and show that an unglycosylated segment of gp120 elicits a neutralizing immune response comparable to that elicited by the virus. As is shown in Table 1, even though it is less than half the size of gp120, PB1 contains epitopes that allow complete neutralization of HIV infection. PB1 stimulates proliferation of lymphocytes from goats immunized with gp120, suggesting that PB1 also contains the regions of gp120 required to bind the T4 molecule.

Figure 1:
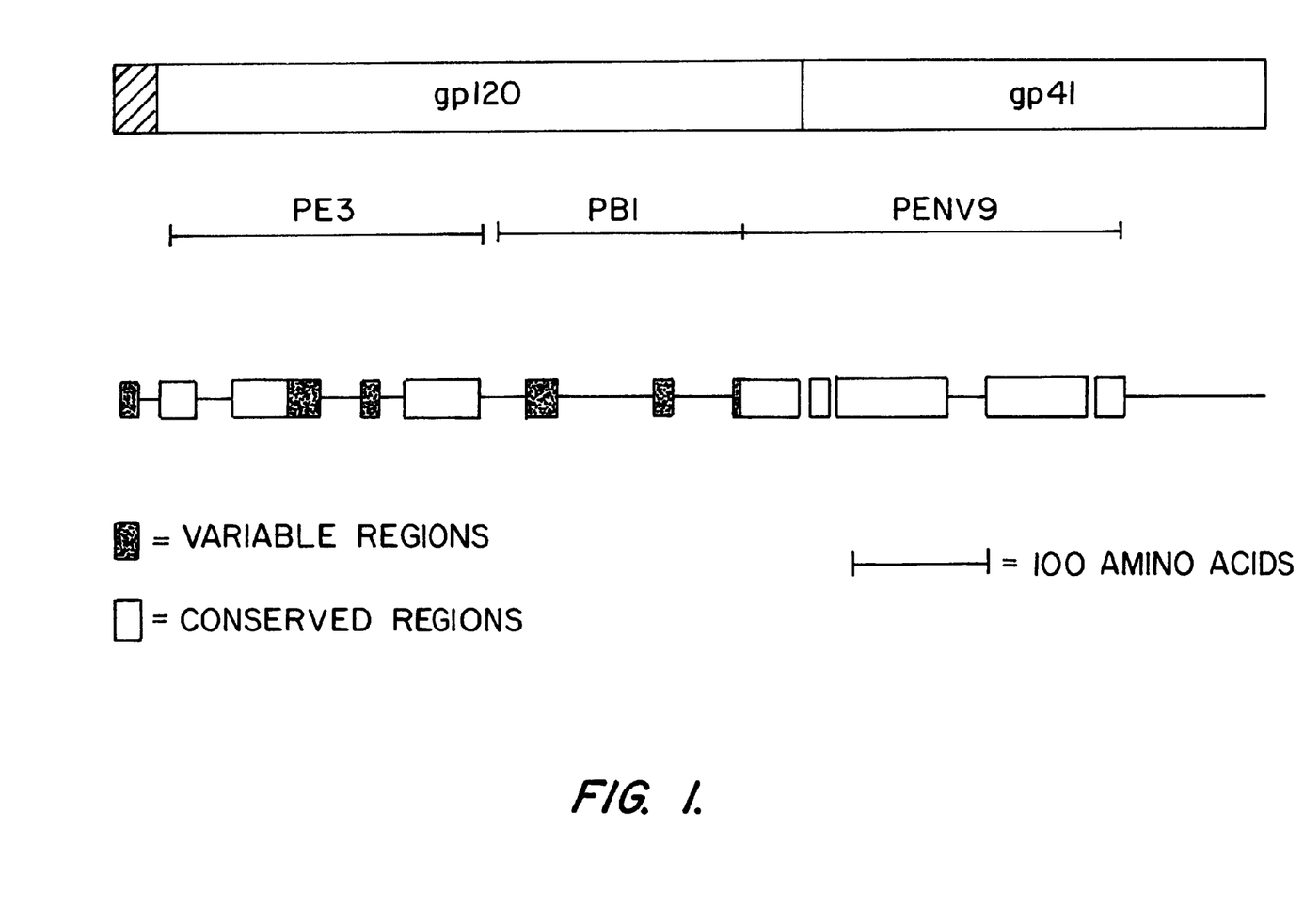
FIG. 1 illustrates the location of recombinant proteins PB1, PE3, and PENV9 in relation to gp120. The secretion signal sequence is hatched; the location of variable and conserved regions are shown as darkened or open boxes, respectively.

Neutralizing type-specificity is presumably caused by differences in the sequence of gp120. The region spanned by PB1 contains three of the five variable regions and none of the three conserved regions of gp120(FIG. 1). It is likely that the variable regions within PB1 play a role in type-specificity, and the first and third of these are predicted to be strongly antigenic. The amino acid sequence variations may present difficulty in the development of a vaccine which neutralizes multiple virus types.

While all of the antigenic proteins of the present invention are useful in the production of vaccines, the recombinantly produced subunit vaccines offer several advantages over more traditional vaccine approaches using killed or attenuated viral preparations. First, recombinant HIV envelope proteins are safer to prepare and administer since no genetic material would be introduced by vaccination. Secondly, purified recombinant envelope fragments are more readily produced than purified gp120isolated from virus-infected cells. For example, 1 milligram of purified gp120 is obtained from 500 grams of infected cells, while approximately 3 grams of purified PB1 can be obtained from 500 grams of E. coli. Finally, because it is produced from a recombinant gene, the sequence of PB1 can be altered by in vitro mutagenesis to obtain a spectrum of synthetic peptides containing neutralizing epitopes.

Blockade of Cell Fusion

One consequence of virus infection is the formation of multinucleated giant cells syncytia which can be mediated by fusion events initiated by the infected cell. It has been shown that the CD4 antigen is an essential component in the reaction in which virus-negative cells (bearing CD4) fuse with infected cells. Sodroski et al, *Nature,* 322:470–474 (1986) shows that the essential components can be limited to the expression of CD4 and virus envelope gene products on the respective cell surfaces. As shown in Example 5, gp120 specifically blocks the CD4 site, thus interfering with virus mediated cell fusion. A gp120 concentration of only about 2 to 4nM is required to completely block the fusion process.

A pharmaceutical composition in accordance with the present invention comprises immunogenic amount of the substantially pure, isolated gp120 or PB1 polypeptide in a pharmaceutically acceptable carrier.

EXAMPLES

Example 1.

Goats were immunized with 2 mg PB1, 1 mg PE3, or 50 $\mu$g Dg-120 and boosted as described above. PE3 is purified in essentially the same manner as PB1 through the extraction step except that 8M urea is used rather than guanidine hydrochloride. The urea is removed by dialysis into tris buffer, pH 7.5, and PE3 purified using two sequential S-30-gel filtration columns (Pharmacia). The purified protein is over 90% homogeneous as judged by SDS-polyacrylamide gels, and the yield is equivalent to that of PB1. The immune sera were tested for reactivity to HIV proteins from virus infected cells on Western Blots and to purified native gp120 by radioimmune precipitation. Antibodies from animals immunized with either PB1, PE3, or DG-120 precipitated gp120 to comparable extents (Table 1). The efficacies of precipitation are equivalent to that of antisera of goat, horse, or rhesus monkeys immunized with native gp120. In addition, sera from HIV infected individuals reacted to a similar extent in a Western analysis with gp120 and DG-120. This showed that the immunogenicity of gp120was independent of glycosylation.

Example 2.

Neutralization of HIV Infection.

Cell-free HIV infection was measured using the H9 clone of the HT cell line. HIV infection was measured by expression sion of either the p24 core protein or reverse transcriptase. The virus (the HTLV-$III_B$ isolate) and diluted sera were reincubated and H9 cells were then added. After 7 to 10 days, p24 was measured by indirect immunofluorescence, using a p24 specific monoclonal antibody or reverse transcriptase was measured by standard enzymatic assay. The amount of reverse transcriptase activity present in a particular assay varied according to when the cells were harvested. Antisera to gp120, DG-120, and PB1 completely blocked infection at a dilution of 1:8, and no effect was seen at a 1:128 dilution.

Neutralizing titers were calculated from the assay described herein supra and were the reciprocal of the serum dilution at which HIV infection was 60% of that using pre-immune serum from the same animal. Neutralizing assays measuring p24 were done as described in Guroff, et al, *Nature,* 316:72–74 (1985). gp120 was purified and radioimmune precipitation assays of $^{125}$I labeled gp120(labeled using chloramine-T) were performed. All preimmune goats precipitated approximately 0.9% of labeled gp120. The neutralizing titers of the sera from rabbits immunized with PB1 were approximately four-fold lower than anti-PB1 goat sera.

Example 3.

The native and deglycosylated forms of gp120 were examined for their ability to bind the CD4 cell surface marker, using several experimental approaches. The CEM T-lymphocyte cell line was used as a target cell because of its high level of CD4 expression at the cell surface. Using a monoclonal antibody to gp120 and monoclonal antibodies OKT4 and OKT4A in conjunction with the fluorescence activated cell sorter (FACS), it was possible to demonstrate direct binding of gp120 to CD4 on the surface of CEM cells in two ways: (1) by enabling the binding of monoclonal anti-gp120 to the cell surface, and (2) by preventing the binding of OKT4A to CD4.

CEM cells ($3\times10^5$/ml) were incubated for 2 hours at 37° C. with 5 $\mu$g/ml gp120 mock digested (no enzyme) in the presence of 0.025% SDS, Endo F digested gp120 in the presence of 0.025% SDS, and HIV p24 (35 µg/ml). The cells were washed in ten volumes of PBS containing 2% fetal calf serum (FCS) and 0.1% sodium azide. One million cells were resuspended in PBS/FCS/azide containing a 1:20 dilution of OKT4, OKT4A, or anti-gp120 monoclonal antibody. Following a 1 hour incubation on ice, the cells were washed in 40 volumes of PBS/FCS/azide and the cell pellets were resuspended in 100 µl of a 1:20 dilution of FITC-conjugated F(ab')2 goat anti-mouse IgG (Cooper Biomedical), and incubated on ice for 1 hour. Finally, cells were washed in approximately 200 volumes of PBS/FCS/azide and resuspended to a concentration of $10^6$ cell/ml. Cytofluorographic analysis was performed using EPICS, Model 753 fluorescence activated cell sorter (Coulter Electronic). The results are plotted in FIG. 2 as relative cell number (y-axis) versus fluorescence Intensity on a linear scale (x-axis). The numbers in the upper right portion of each panel indicate the % positive cells/mean fluorescent channel.

Figure 2:
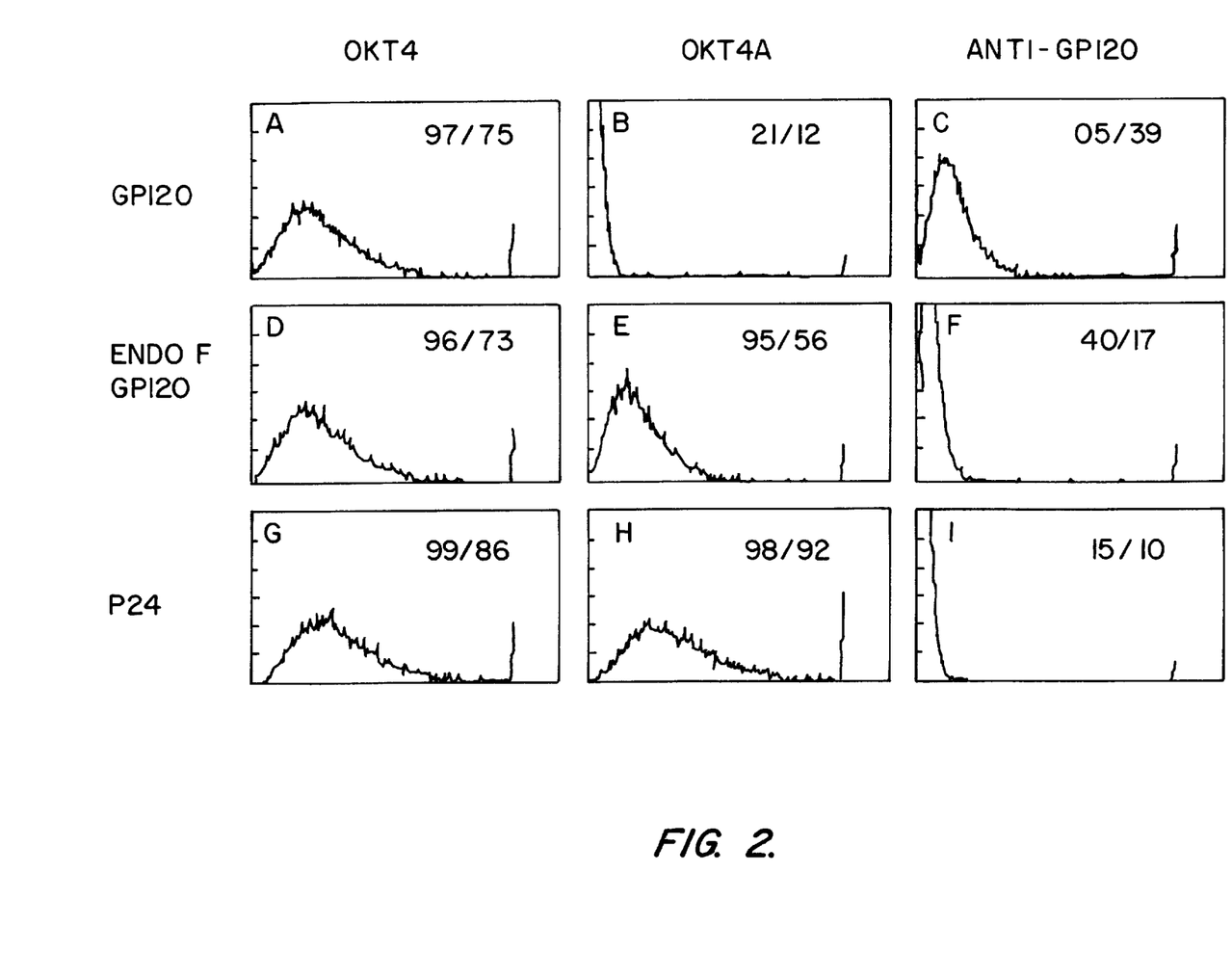
FIG. 2 shows the binding of gp120 and DG120 (Endo F gp120) to uninfected CEM cells.

The results demonstrate that attachment of monoclonal anti-gp120to CEM cells occurred only following pre-incubation with gp120. A control viral polypeptide, p24, did not mediate binding (Panel I). Moreover, the binding of gp120 to CEM specifically blocked the epitope on CD4 recognized by OKT4A, but not OKT4 (compare panels A and B to panels G and H). The fully deglycosylated form of gp120, DG120, lost a major portion of its binding capacity to CEM, as evidenced by both the lack of binding to monoclonal anti-gp120 (panels C and F), and its failure to block the binding of OKT4A (panels B and E). The loss of binding activity in the DG120 was apparently not due to denaturation by SDS, since the same level of SDS had no effect on the binding of native gp120. In other assays, the monoclonal anti-gp120 was found to bind DG120 with the same efficacy as the native molecule.

Example 4.

Figure 3:
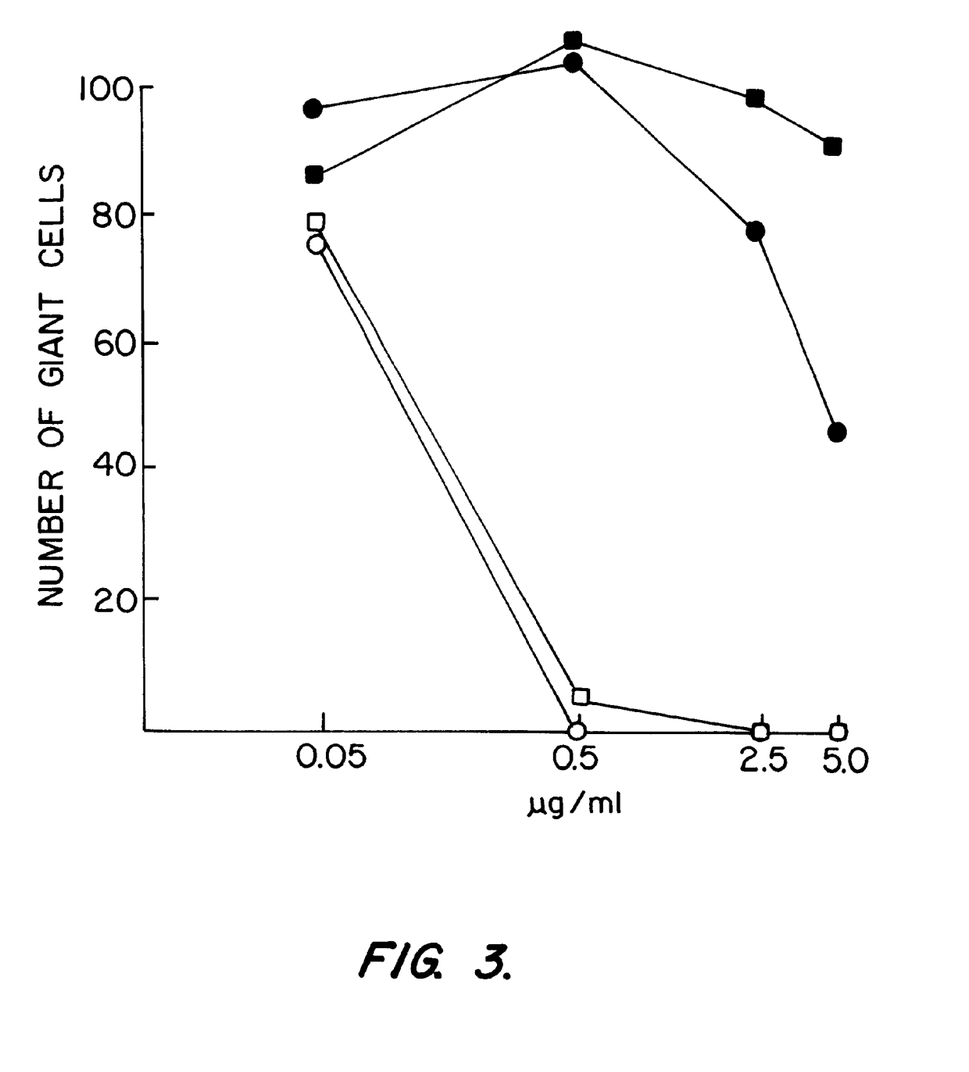
FIG. 3 illustrates the ability of gp120 and DG120 to block multi-nucleated giant cell formation mediated by chronically infected CEM cells.

The ability of gp120to interfere with the processes of virus infection and virus mediated cell fusion was also determined. A sensitive and quantitative assay for cell fusion was made possible through the development of a stable line of CEM cells infected with HTLV-III$_B$. About 75,000 non-infected CEM cells in a volume of 50 µl were incubated with dilutions of test antigens for 30 minutes at 37° C. in 96 one-half area wells. About 5,000 CEM cells (50 µl) chronically infected with HTLV-III$_B$ were added to each well and the samples were incubated for 24 hours at 37° C. Within this time period, giant cell formation could be seen evenly dispersed throughout the surface of each well. These cells had a diameter in excess of 5-fold that of CEM or chronically infected CEM cells, and appeared in numbers which were proportional to the inoculation of infected cells. The number of giant cells per well was estimated by microscopic examination (40×magnification) and recorded as shown in FIG. 3. The four antigens tested include HTLV-III$_B$p24; DG120 (gp120digested with Endo F in the presence of SDS); o mock digested (no enzyme) gp120 with the same level of SDS; and DG120 (in the absence of SDS).

When infected CEM cells were mixed with their uninfected counterparts, easily visualized and enumerated multi-nucleated giant cells were formed within 24 hours. While purified gp120 alone was not able to mediate cell fusion (when added to uninfected CEM cells), it was a very effective inhibitor of the fusion mediated by infected CEM cells. Its blocking effect was so complete that as little as 500 ng/ml of gp120 could completely inhibit the process (FIG. 3). In contrast, DG120 displayed a 50-fold reduction in efficacy. These results are consistent with the binding activities noted for each form of the antigen, suggesting that some, but not all of the carbohydrate present on native gp120, is necessary for binding and biological activity.

Example 5.

The ability of native gp120derived from HTLV-III$_B$ to prevent the fusion of CEM cells infected with other virus isolates was also tested. A stable CEM cell line infected with HTLV-III$_{RF}$ was used for this purpose because this isolate exhibits a 20% divergence in the amino acid sequence of the gp120 portion of the envelope gene. As shown in Table 2, the gp120 of HTLV-III$_B$ was equally effective in its ability to prevent cell fusion mediated by HTLV-III$_B$ and HTLV-III$_{RF}$ infected CEM. In a like manner, gp120 of HTLV-III$_B$ interfered with infection of CEM by both the HTLV-III$_B$ and HTLV-III$_{RF}$ isolates, although the degree of interference relative to cell fusion was not as pronounced.

About 75,000 CEM cells were placed in CoStar A/2 wells. For the virus infection study, about 50 infectious units of HTLV-III$_B$ and HTLV-III$_{RF}$ were added per well in the absence and presence of HTLV-III$_B$ gp120 (5 µg/ml). Both virus isolates had been propagated and titrated in H9 cells. The cultures were maintained for two weeks by doubling the medium (RPMI 1640 plus 10% FCS) on a daily basis. Virus Infection was based on the level of viral p24 antigen released to the supernatant of the cultures using a competition radioimmunoassay. For the cell fusion study, 5,000 CEM cells chronically infected with either HTLV-III$_B$ or HTLV-III$_{RF}$ were added to duplicate wells containing the uninfected CEM cells in the absence or presence of HTLV-III$_B$ gp120(5 µg/ml). The average number of giant cells in duplicate wells was enumerated as described above. Giant cells were not evident in subcultures of wells maintained for an additional 3 days in the presence of gp120 (see Table 2 for the specific results obtained).

Example 6.

Goat. horse, and rhesus monkey (Macaca mulatta) immune sera were prepared using either the water soluble fraction from the dialyzed immunoaffinity column eluate (goat and rhesus) or PAGE-purified gp120 (goat and horse). The primary and secondary intramuscular immunizations consisted of 50 µg (goat) or 100 µg (horse) of soluble protein or protein Immobilized in acrylamide gel emulsified with Freund's complete adjuvant. The secondary immunization was 21 days following the last immunization. The rhesus monkeys were immunized with three doses of 20 µg of soluble gp120 emulsified with threonylmuramyl dipeptide. The primate immunizations were intramuscular and spaced 21 days apart. The results shown in Table 3 indicate that antiserum directed against gp120 precipitated the homologous protein, and that early bleed sera from all of the immunized animals contained antibodies capable of neutralizing HIV infection of H9 cells in vitro. The 50% inhibition titers for the animal immune sera ranged from 1:20 to 1:60 compared to 1:40 obtained from an AIDS patient serum tested under the same conditions. In short, the purified external glycoprotein elicits a virus neutralizing humoral response equivalent to the response observed in at least one human patient.

Example 7.

Figure 4:
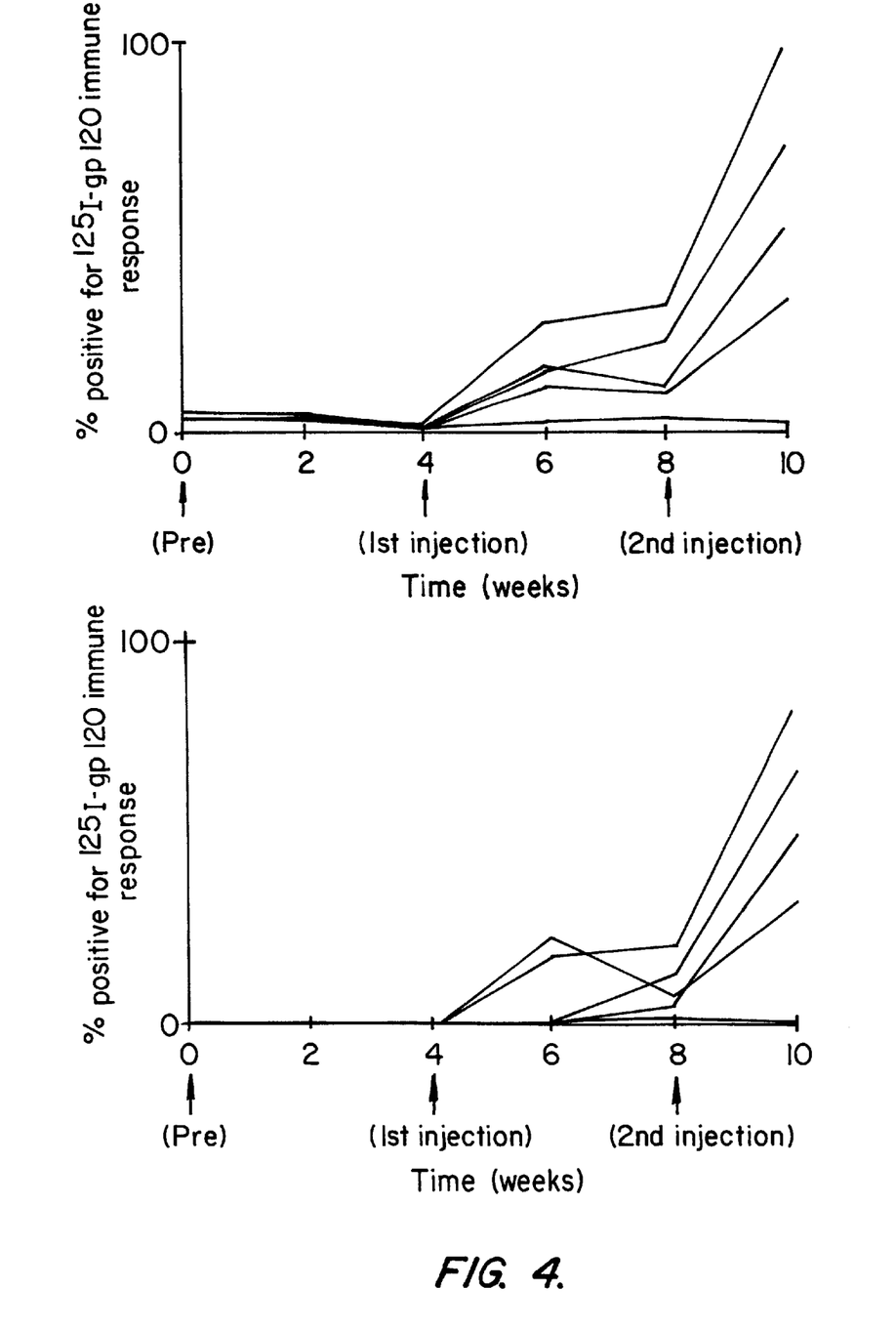
FIG. 4 illustrates antibodies binding to gp120 in immunized chimpanzees.

Chimpanzees were immunized with gp120 In an inert carrier to determine if the glycoprotein of the present invention establishes a protective humoral immunity to HIV in vivo. FIG. 4 shows that after the third vaccination all of the chimpanzees were positive for immune response as indicated by $^{125}$I-gp120 immunoprecipitates.

Example 8.

Demonstration of the expression of gp160 on infected insect cell membrane immunofluorescence. Infected and non-infected insect cells were washed with PBS and incubated for 30 minutes at +4° C. with 1:100, 1:200, and 1:500 dilutions of primary antisera. After washing twice with PBS, fluorescein thiocyanate conjugated to secondary antisera in 2 1:200 dilution was added [Fc-specific Fab fragments of FITC labeled rabbit anti-goat for the goat antisera, and FITC labeled rabbit anti-mouse for the anti-C7 monoclonal antibody (both from Cappel Laboratories)]. The results are shown below:

|  |  | INSECT CELLS | |
|---|---|---|---|
| GOAT | IMMUNOGEN | INFECTED | NON-INFECTED |
| 517, 2935 | gp120 | +++ | − |
| 987, 988 | PB1 | + | − |
| Anti-C7 | C7 | − | − |
| 993, 994 | gp160 | +++ | − |
| 980, 992 | inf. cells | ++ | +++ |

(+++) = intense membranous stain;
(++) = moderate staining;
(+) = weak staining;
(−) = negative.

Example 9.

The first evidence of broad neutralizing capacity of the goat sera against purified gp120 or against infected cells (i.e. neutralization of the cytolytic effect of HTLV-III isolates by goat sera) was shown by an assay method in which a highly sensitive T-helper cell line (ATH8) was used as a target cell for HTLV-III induced cytolysis. Three different HIV virus isolates—HTLV-III$_B$, HTLV-III$_{MN}$, and HTLV-III$_{RF}$ with major differences in the nucleotide sequences of the envelope gene were used. The neutralizing capacity of goat sera against the purified pg160 was similar to that observed with a goat serum against purified native gp120. Most importantly, the anti-gp160 sera also showed group specific neutralizing capacity against viral isolates MN and RF, although the strongest activity was against the HTLV-III$_B$, the strain from which the expressed clone was derived.

|  |  | HTLV-III STRAIN USED | | |
|---|---|---|---|---|
| GOAT | IMMUNOGEN | III$_B$ | III$_{MN}$ | III$_{RF}$ |
| 990 | inf. cells | 0* | 0 | 0 |
| 992 | inf. cells | 0 | 0 | 0 |
| 993 | gp160 | 320 | 40 | 0 |
| 994 | gp160 | 640 | 80 | 20 |
| 987 | PB1 | 40 | 0 | 0 |
| 988 | PB1 | 80 | 0 | 0 |
| 517 | gp120 | 160 | 0 | 0 |

*reciprocal of serum dilution giving 100% protection of cytolysis of ATH8 cells, induced by 100 TCIU$_{50}$ of the virus.

ATH8 cells were cultured with RPMI-1640, 10% FCS, and 10% IL-2 on 96-well microtiter plates (50,000 cells/well at the beginning of the culture period) with and without 100 TCEW$_{50}$ of the various HTLV-III strains. In addition, cultures contained no serum of various dilutions of the test sera. Cultures were fed at 3 and 7 days, and the cytotoxic effect was assessed by visual inspection after 10 days of culture.

Example 10.

The table below shows the comparative results of T-cell proliferation indicative of the level of cellular immune response to gp120, immunizations with PB1 and gp160, with all three HIV virus isolates tested in goats. The broad, group specific nature of the T-cell response is clearly demonstrated with the antigens. Goats 993 and 994, immunized with purified gp160 from HTLV-III$_B$, expressed a group specific T-cell response towards all three HTLV-III isolates. These results were similar to, but weaker than, that observed in the goat immunized with native gp120. In contrast, goat 990 and 992, immunized with infected cells, did not express any T-cell response.

|  |  | HTLV-III isolates | | | gp120 | |
|---|---|---|---|---|---|---|
| GOAT | IMMUNOGEN | B | MN | RF | B | RF |
| 517 | gp120 | 110 | 120 | 100 | 100 | 65 |
| 990 | inf. cells | <1 | 1.3 | 1.1 | <1 | 1.8 |
| 992 | inf. ceils | 1.6 | 1.6 | 1.4 | 2.2 | 1.0 |
| 993 | gp160 | 6 | 2 | 5 | 5 | 4 |
| 994 | gp160 | 9 | 25 | 12 | 40 | 25 |
| 987 | PB1 | <2 | <2 | <2 | <2 | <2 |
| 988 | PB1 | <2 | <2 | <2 | <2 | <2 |

T-cell proliferative responses of goat lymphocytes expressed as stimulation indices (cpm with test antigen: cpm without test antigen), of peripheral blood mononuclear cells stimulated with heat killed whole HTLV-III isolates or with purified envelope glycoprotein gp120.

Tables 4–5 show additional comparative results obtained with gp120 and PB1.

It is understood that the examples and embodiments described herein are for illustrative purposes only and that various modifications or changes in light thereof will be suggested to persons skilled in the art and are to be included within the spirit and purview of this application and scope of the appended claims.

TABLE I

HIV Neutraliting Antibodies and gp120
Precipating Efficacies of Goat Immune Sera
HIV Neutralizing Titers

| Goat Serum and Immunogen | % Labeled gp120 Precipitated | Indirect Immuno-fluorescence of p24 | Reserve Transcriptase |
|---|---|---|---|
| 987 (PB1) | 19 | 25 | 25 |
| 988 (PB1) | 18 | 60 | 20 |
| 517 (gp120) | 29 | 50 | 30 |
| 508 (DG-120) | 37 | 50 | 30 |
| 542 (PE3) | 38 | 0 | N.T. |
| Preimmune Goat | 0.9 | — | — |

N.T. = not tested

TABLE 2

| Virus Infection | | | | Cell Fusion | | |
| --- | --- | --- | --- | --- | --- | --- |
| | p24(ng/ml) | | | | Number of Giant Cells | |
| Day | gp120 | HTLV-III$_B$ | HTLV-III$_{RF}$ | Day | gp120 | CEM/III$_B$ | CEM/III$_{RF}$ |

| Day | gp120 | HTLV-III$_B$ | HTLV-III$_{RF}$ | Day | gp120 | CEM/III$_B$ | CEM/III$_{RF}$ |
| --- | --- | --- | --- | --- | --- | --- | --- |
| 6 | − | 30 | 1 | 2 | − | 73 | 64 |
|   | + | 3 | 0 |   | + | 0 | 0 |
| 8 | − | 100 | 15 | 4 | − | 55 | 85 |
|   | + | 74 | 1 |   | + | 0 | 0 |
| 9 | − | N.T. | 60 | | | | |
|   | + | N.T. | 11 | | | | |
| 14 | − | 150 | 160 | | | | |
|   | + | 170 | 110 | | | | |

TABLE 3

Neutralization of HIV by Sera That Contain Antibodies to gp120
Reverse transcriptase levels *
at three serum dilutions

| Serum | 1:10 | 1:40 | 1:160 | Inhibition Titers |
| --- | --- | --- | --- | --- |
| Coat anti-gp120 (native) | 6,400 | 141,000 | 100,000 | 1:20 |
| Goat pre-immune for above | 136,000 | 104,000 | 86,000 | |
| Rhesus anti-gp120 (native) | 5,900 | 83,400 | 107,600 | 1:30 |
| Rhesus pre-immune for above | 112,700 | 122,100 | 99,800 | |
| Goat anti-gp120 (PAGE) | 2,100 | 3,600 | 168,000 | 1:60 |
| Goat pre-immune for above | 118,000 | 103,000 | 92,000 | |
| Horse anti-gp120 (PAGE) | 2,300 | 105,400 | 69,800 | 1:30 |
| Horse pre-immune for above | 91,300 | 67,700 | 82,000 | |
| Human AIDS patient | 1,800 | 86,000 | 130,000 | 1:40 |

* cpm of Mg$^2$-dependent reverse transcriptase detected in virus pellets.
The inhibition titers were determined graphically from the above values.

TABLE 5

Cellular immune response towards recombinant HIV envelope proteins (PB1, R10, 590 and gp160) in chimpanzees immunized with native gp120$_{IIIB}$ or with recombinant protein PB1.

| ANIMAL NO. | IMMUNE STATUS | PROLIFERATIVE RESPONSE (STIMULATION INDEX*) | | | | IL-2 SECRETION** | |
| --- | --- | --- | --- | --- | --- | --- | --- |
| | | PB1 | R10 | 590 | gp160 | PB-1 | gp160 |
| 1 (888) | Control | 1 | 1 | 1 | 1 | 2 | 7 |
| 2 (963) | Control | 1 | 1 | 1 | 1 | 3 | 3 |
| 3 (1041) | gp120 | 5 | 4 | 3 | 7 | 15 | 14 |
| 4 (1052) | gp120 | 16 | 15 | 16 | 23 | 93 | 92 |
| 5 (1053) | gp120 | 4 | 6 | 4 | 2 | 0 | 3 |
| 6 (1068) | gp120 | 17 | 54 | 51 | 45 | — | — |
| 7 (1086) | gp120 | 255 | 230 | 43 | 136 | 6 | 3 |

TABLE 4

Cellular immune response towards three divergent heat inactivated HIV-1 virion preparations (HTLV-III$_B$, HTLV-III$_{MN}$ and HTLV-III$_{RF}$) and towards homologous native envelope glycoprotein (gp120$_{IIIB}$) and neutralizing antibody titers in chimpanzees immunized with gp120$_{IIIB}$ or with recombinant protein PB1.

| ANIMAL NO. | IMMUNE STATUS | PROLIFERATIVE RESPONSES (STIMULATION INDEX*) | | | | IL-2 SECRETION** | | NEUTRAL. ANTIBODY TITER*** |
| --- | --- | --- | --- | --- | --- | --- | --- | --- |
| | | B | RF | MN | gp120 | IIIB | gp120 | |
| 1 (888) | Control | 1 | 1 | 1 | 1 | 0 | 0 | 0 |
| 2 (963) | Control | 1 | 1 | 1 | 1 | 0 | 2 | 0 |
| 3 (1041) | gp120 | 2 | 2 | 1 | 3 | 0 | 4 | 320 |
| 4 (1052) | gp120 | 13 | 10 | 7 | 47 | 2 | 56 | 40 |
| 5 (1053) | gp120 | 2 | 2 | 2 | 3 | 1 | 5 | 40 |
| 6 (1068) | gp120 | 20 | 2 | 10 | 18 | 7 | 34 | 160 |
| 7 (1086) | gp120 | 150 | 100 | 60 | 400 | 37 | 48 | 320 |
| 8 (1113) | gp120 | 35 | 10 | 8 | 39 | 5 | 46 | 160 |
| 9 (1125) | gp120 | 48 | 22 | 20 | 35 | 4 | 1 | 160 |
| 10 (1345) | gp120 | 12 | 20 | 4 | 16 | 5 | 68 | 160 |
| 11 (902) | PB1 | 5 | 4 | 6 | 3 | 3 | 35 | 320 |
| 12 (903) | PB1 | 12 | 17 | 15 | 13 | 5 | 92 | 1280 |
| 13 (1110) | PB1 | 10 | 8 | 9 | 5 | 3 | 43 | 640 |
| 14 (1141) | PB1 | 13 | 11 | 23 | 8 | 32 | 332 | 160 |

*Stimulation Index = counts per minute (cpm) with optimal dose of antigen/cpm without antigen.
**IL-2 Secretion = Unit/ml of IL-2 in the supernatant of five days culture with optimal dose of antigen.
***Peciprocal of the highest dilution of serum giving >80% protection for HTLV-III$_B$ induced cytolysis of ATH8 cells.

TABLE 5-continued

Cellular immune response towards recombinant HIV envelope proteins (PB1, R10, 590 and gp160) in chimpanzees immunized with native gp120$_{IIIB}$ or with recombinant protein PB1.

| ANIMAL NO. | IMMUNE STATUS | PROLIFERATIVE RESPONSE (STIMULATION INDEX*) | | | | IL-2 SECRETION** | |
|---|---|---|---|---|---|---|---|
| | | PB1 | R10 | 590 | gp160 | PB-1 | gp160 |
| 8 (1113) | gp120 | 31 | 24 | 10 | 34 | 46 | 51 |
| 9 (1125) | gp120 | 84 | 80 | 100 | 90 | — | — |
| 10 (1345) | gp120 | 68 | 271 | 176 | 117 | 4 | 3 |
| 11 (902) | PB1 | 30 | 37 | 20 | 10 | 7 | 2 |
| 12 (903) | PB1 | 32 | 18 | 17 | 15 | 61 | 83 |
| 13 (1110) | PB1 | 9 | 6 | 3 | 2 | 2 | 1 |
| 14 (1141) | PB1 | 54 | 72 | 46 | 23 | 100 | 138 |

*Stimulation Index = cpm with optimal dose of antigen/cpm without antigen.
**IL-2 secretion = Unit/ml if IL-2 in the supernatant of five days culture with optimal dose of antigen.

What is claimed is:

1. An HIV polypeptide PB1, consisting of an amino acid sequence as shown in FIG. 5.

2. A composition comprising an immunogenic amount of the polypeptide of claim 1 and a pharmaceutically acceptable carrier.

3. A method of eliciting an immune response, the method comprising administering to a responsive host an immunogenic amount of the polypeptide of claim 1 to induce an anti-HIV immune response.

4. A method of producing, in a mammal, antibodies that neutralize HIV, the method comprising administering to said mammal an amount of the polypeptide of claim 1 sufficient to effect said production.

5. An HIV polypeptide PB1 comprising the amino acid sequence encoded by a PvuII to BgIII fragment of an HIV env gene.

6. An immunogenic composition comprising a polypeptide having the antigenic properties of a polypeptide according to claim 5.

7. An immunogenic composition comprising a hybrid PB1 polypeptide having the amino-acid sequence of a PB1 polypeptide from different HIV isolates.

8. An immunogenic composition according to claim 7, wherein the HIV isolates are HIV$_B$, HIV$_{MN}$, and HIV$_{RF}$.

* * * * *